(12) United States Patent
Reeslev et al.

(10) Patent No.: US 7,939,285 B2
(45) Date of Patent: May 10, 2011

(54) FILTRATION METHOD FOR DETECTING MICROBIAL CONTAMINATION

(75) Inventors: Morton Reeslev, Copenhagen Ø (DK); Morten Miller, Copenhagen Ø (DK)

(73) Assignee: Mycometer APS, Copenhagen (DK)

( * ) Notice: Subject to any disclaimer, the term of this patent is extended or adjusted under 35 U.S.C. 154(b) by 745 days.

(21) Appl. No.: 10/591,321

(22) PCT Filed: Feb. 28, 2005

(86) PCT No.: PCT/DK2005/000137
§ 371 (c)(1),
(2), (4) Date: Aug. 31, 2006

(87) PCT Pub. No.: WO2005/083109
PCT Pub. Date: Sep. 9, 2005

(65) Prior Publication Data
US 2007/0178446 A1 Aug. 2, 2007

Related U.S. Application Data

(60) Provisional application No. 60/549,158, filed on Mar. 3, 2004.

(30) Foreign Application Priority Data

Mar. 1, 2004 (DK) .................................. 2004 00348

(51) Int. Cl.
*G01N 33/53* (2006.01)
*G01N 1/18* (2006.01)
*C12Q 1/02* (2006.01)

(52) U.S. Cl. .......................... 435/7.72; 435/29; 436/177

(58) Field of Classification Search .................. None
See application file for complete search history.

(56) References Cited

U.S. PATENT DOCUMENTS

| | | | |
|---|---|---|---|
| 4,591,554 A * | 5/1986 | Koumura et al. ............... | 435/18 |
| 4,871,662 A | 10/1989 | Rosov | |
| 5,081,017 A * | 1/1992 | Longoria ........................ | 435/30 |
| 5,089,395 A | 2/1992 | Snyder et al. | |
| 5,518,894 A | 5/1996 | Berg | |
| 5,610,029 A | 3/1997 | Ehrenfeld et al. | |
| 5,714,343 A * | 2/1998 | Tuompo et al. ................. | 435/29 |
| 5,741,659 A * | 4/1998 | Ralls et al. ...................... | 435/23 |
| 5,811,251 A | 9/1998 | Hirose et al. | |
| 5,854,011 A * | 12/1998 | Chen et al. ...................... | 435/24 |
| 5,968,762 A | 10/1999 | Jadamec et al. | |
| 6,090,573 A * | 7/2000 | Laine et al. ..................... | 435/32 |
| 6,517,593 B1 | 2/2003 | Robertson et al. | |
| 2004/0219628 A1 | 11/2004 | Tashiro et al. | |

FOREIGN PATENT DOCUMENTS

| | | |
|---|---|---|
| EP | 0122581 | 1/1991 |
| EP | 0574977 | 1/1997 |
| JP | 08-140698 | 6/1996 |
| WO | 2003/012397 | 2/2003 |

OTHER PUBLICATIONS

International Search Report (PCT/ISA210) and (PCT/ISA/220), Jun. 29, 2005.

\* cited by examiner

*Primary Examiner* — Rebecca E. Prouty
*Assistant Examiner* — Paul C. Martin
(74) *Attorney, Agent, or Firm* — Harness, Dickey & Pierce, P.L.C.

(57) ABSTRACT

Disclosed is a convenent sample preparation method for a medium suspected of containing contaminants, the method comprising a) passing a known volume of said medium through a filter from an influent side to an effluent side thereby concentrating the contaminants on the influent side of the filter, b) contacting the influent side of the filter with a liquid vehicle containing at least one substrate that through interaction with the contaminants each produces a detectable moiety, c) and allowing the substrate to interact with the contaminants on the influent side of the filter for a period of time, which is sufficient to allow the detectable moiety to be detected in the liquid vehicle. The method may further comprise a detection step, where the amount of detectable is determined in the liquid vehicle, preferably after the liquid vehicle has been separated from the contaminant, e.g. by passing the liquid vehicle through the filter and performing a measurement on the contaminant free liquid vehicle. Also disclosed is a kit for exercising the inventive method.

50 Claims, 3 Drawing Sheets

FILTRATION METHOD FOR DETECTING MICROBIAL CONTAMINATION

Figure 1:
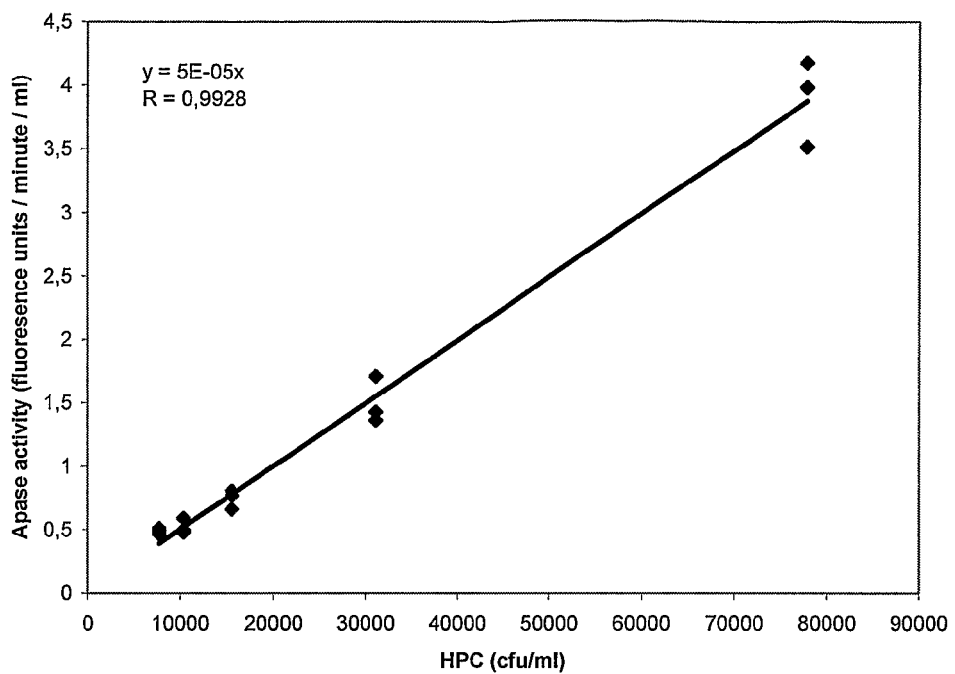

This application claims the benefit of priority under 35 U.S.C. §119(e) to U.S. Provisional application 60/549,158 filed Mar. 3, 2004.

FIELD OF THE INVENTION

The present invention relates to the field of environmental surveillance and control, especially to the determination of contaminants in environmental samples. More specifically, the invention relates to a simple, versatile, robust, reliable, and rapid method that provides a precise measurement of (microbial) contamination, which can be carried out in situ. The invention further provides for a kit, which is useful for performing such measurements.

BACKGROUND OF THE INVENTION

To address the problem of bacterial contamination, several test methodologies have been developed. The classical methods are based on cultivation of bacteria on a nutrient media supporting growth. After approximately 2-14 days, bacteria capable of growing on solid medium have multiplied to a level where colonies become visible and can be counted, and bacteria capable of growing in fluid medium can be measured by e.g. optical density or dry weight. Efforts have been made to expedite and simplify the detection process. Among these efforts have been methods based on measurements of radiometry, impedance, chemiluminiscence and fluorescence.

Radiometric approaches for identifying bacterial contamination generally utilize incorporation of a radioactive nutrient by the bacteria. The radiolabelled bacteria can be isolated and quantified by following the radiolabel. This methodology has several undesirable drawbacks. Although very sensitive, it utilizes radioisotopes which can be expensive and difficult to handle.

Methods based on electrical impedance typically include a cultivation step. As the microorganisms grow, changes in impedance of the nutrient medium can be detected and correlated to the microbial growth. Methods based on electrical impedance, although more rapid than classical cultivation, are still slow, involving an incubation period of 1-4 days.

ATP is detected by chemiluminiscence. Detection and/or quantification of bacteria by use of detection of ATP is rapid and can be performed within minutes. However, ATP is ubiquitous and the kinetics of ATP-derived luminescence is complex, qualities that lowers the robustness of methods based on this principle. Furthermore, the turnover of ATP in the cells is very rapid and the ATP content of cells may experience huge variations in a short time period e.g. when cells goes from growth to starvation.

Several methods have been described in the prior art based on the enzymatic degradation of a fluorescently labelled umbelliferone substrate with concomitant monitoring of the fluorescence derived from the released umbelliferone. Detection or quantification of bacteria by use of enzyme activity may also be susceptible to interference from non-bacterial sources although this interference appears less significant. Furthermore, the amount of product (fluorescence) formed per time unit is linear. Minimized interference and simple kinetics render measurements of bacteria by use of enzyme activity more robust.

U.S. Pat. No. 4,591,554 (Koumura et al.) discloses a method for rapidly detecting microorganisms utilizing nonfluorescent umbelliferone derivatives such as 4-methyl-umbelliferyl-β-D-galactoside, 4-methyl umbelliferyl-α-D-galactoside, 4-methyl umbelliferyl-phosphate, and 4-methyl umbelliferyl-pyrophosphate. Fluorescence of the liberated umbelliferone moiety is induced at 360 nm and monitored at 450 nm. Enhancement of sensitivity is obtained through a cultivation step for 1-12 hours.

U.S. Pat. No. 5,518,894 (Berg) discloses a rapid method to detect the presence of coliform bacteria. This method comprises a concentration step (filtration) in combination with a cultivation step to increase the number of target bacteria present. The fluorescence of hydrolysed umbelliferone derivative is monitored as an indication of the presence of coliform bacteria.

U.S. Pat. No. 5,610,029 (Ehrenfeld et al.) discloses a culture medium for the detection of presence or absence of target microorganisms in a sample. This culture medium includes various nutrients and growth factors, as well as a fluorescent metabolite (4-methyl umbelliferyl-β-D-glucuronide).

All the above mentioned methods based on detection of fluorogenic detection of enzyme activity, utilises a cultivation step which typically leads to a total performance time of 6-72 hours, which in many cases do not satisfy the demands for performance of a rapid method, let alone a method which is performed in situ.

U.S. Pat. No. 5,089,395 (Snyder et al.) discloses use of a nonfluorescent umbelliferone derivative which is enzymatically converted to a fluorescent product to detect the presence of bacteria. In this method there is no cultivation or concentration step. Due to the lack of these steps, the method is not highly sensitive and needs a high concentration of bacteria of a least 1000 /ml and typically higher concentration are acquired.

U.S. Pat. No. 5,968,762 (Jadamec et al.) discloses a method that uses a nonfluorescent umbelliferone derivative which is enzymatically converted to a fluorescent product to detect the presence of bacteria. The invention relates to measuring the fluorescent intensity ratio of the metabolised fluorescent product at a specific wavelength to the metabolizable fluorescent conjugate at a second specific wavelength. A detection time of approx. 80 min for detecting a concentration of 310 (cfu/ml) is given (cfu=colony forming unit).

Membrane filtration of liquid samples is commonly used for investigating liquid samples for bacteria. The sterile membrane filter is placed in a closed device which can be sterilized and the bacteria are collected on the filter. The filter can then be placed on an agar-containing nutrient medium where the colonies can be enumerated following a cultivation process. The filter may also be treated with a fluorogenic dye which is incorporated into the bacteria which then can be enumerated by laser induced fluorescence. All microbiologists who use membrane filtration are familiar with the care that needs to be taken in order to secure a sterile handling the filters. When detecting small numbers of bacteria a filtration step may easily introduce pollutions rendering the process unreliable and highly dependent on operator skill.

Accordingly, what is needed in the art is a rapid method to detect the presence of bacteria in a sample that is simple to perform, robust and reliable.

OBJECT OF THE INVENTION

The object of the present invention is to address a number of the above-referenced drawbacks and shortcomings in the prior art by providing a fast, reliable, versatile and robust method for determining the presence of microorganisms and other contaminants in a sample.

SUMMARY OF THE INVENTION

The present invention is based on the surprising demonstration that a cultivation step as described above may be completely excluded if instead performing an effective step of concentration of microorganisms by means of filtration or methods analogous to filtration. This involves two major advantages over the prior art as it 1) increases the sensitivity, thus allowing significant reductions in the detection time and 2) eliminates compounds or particles in the sample which may interfere in e.g. a fluorogenic detection due to quenching or autofluorescence or in a immunodetection due to cross-reacting substances derived from the culture medium.

The present invention typically utilises a disposable closed filtration unit that would not be applicable if the filtration was to be followed by cultivation or by laser counting. The present invention provides easy, robust and reliable handling of the sterility of the samples during the whole process of analysis. This makes it ideal as a portable field method.

The microorganisms and other contaminants can be concentrated from a large volume which renders possible rapid detection of even very low concentrations—in fact, the method's sensitivity is exclusively set by the minimum number of contaminants that has to be retained by the filter and by the physical properties of the filter, i.e. the size of volumes that can be passed through the filter while preserving the structural integrity thereof. Hence, it is a significant aspect of the present invention that there is no lower limit to the required bacterial concentration in the liquid in order to quantify the amount of viable microbial target populations/bacteria. Thus the method can be used to detect bacteria in a liquid with an amount of at the most 1000 bacteria/ml, but lower amounts are possible, such as most 100 bacteria/ml, at most 10 bacteria/ml and even less than 1 bacteria/ml.

The present invention e.g. allows quantification of microorganisms from samples collected from various sources and in various forms. The sample may be liquid; e.g. drinking water, hot water, etc., industrial water e.g. process water and cleaning in place (CIP) water samples, pharmaceutical water, 2) air; e.g. indoor air, industrial air, air from heavily contaminated work environments, air from pharmaceutical production facilities 3) extractable solid samples; e.g. food stuffs, sediments and plant material etc. 4) surfaces; e.g. building surfaces, construction materials and work surfaces etc.

Hence, in its broadest and most general scope, the present invention relates to a sample preparation method for a medium suspected of containing contaminants, the method comprising a) passing a known volume of said medium through a filter from an influent side to an effluent side thereby concentrating the contaminants on the influent side of the filter, b) contacting the influent side of the filter with a liquid vehicle containing at least one substrate that through interaction with the contaminants each produces a detectable moiety, c) and allowing the substrate to interact with the contaminants on the influent side of the filter for a period of time, said period of time being sufficient to allow the detectable moiety to be detected in the liquid vehicle.

Also part of the invention is a kit for determination of contaminants in a medium, the kit comprising 1) at least one sterile filter device comprising a filter with a pore size sufficiently small to retain the contaminants on the filter's influent side, 2) means for passing a known volume of medium through the filter, 3) an agent that upon interaction with the contaminants will release a detectable moiety, the amount of which can be correlated with the amount of contaminants that have interacted with the agent, and 4) instructions that sets forth steps for a) obtaining a known volume of medium and passing it through the sterile filter device, b) contacting the influent side of the filter with the agent, c) allowing the agent to interact with contaminants that might be on the influent side of the filter, and d) quantitatively detecting the detectable moiety.

Finally, the invention also relates to the use of a closed, sterile filter device as a reaction vessel for a reaction between contaminants retained in the device and a substrate that releases a detectable moiety when contacted with the contaminants.

LEGEND TO THE FIGURE

FIG. 1: Graph showing linear relationship between calculated heterotrophic plate counts (HPC) in a drinking water dilution series, reported as colony forming units per ml water sample, and alkaline phoshatase activity (APase activity), as determined by the fluorescence produced by enzymatic cleavage of the APase substrate 4-methylumbelliferyl phosphate, reported as fluorescence units/min/ml.

Figure 2:
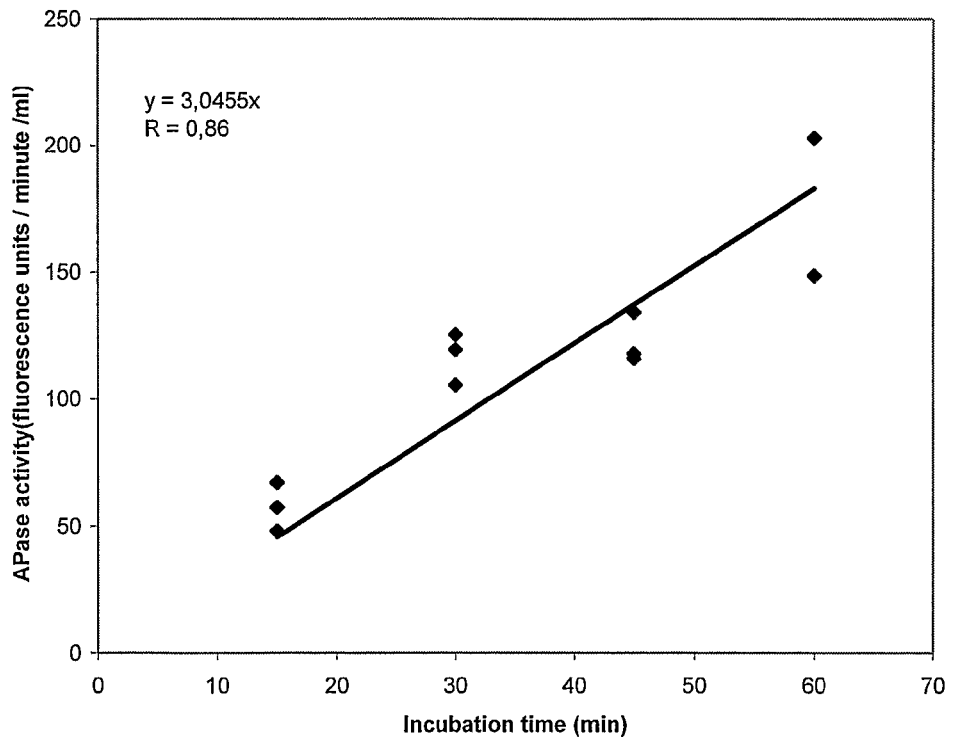

FIG. 2: Graph showing linear relationship between incubation time and APase activity as determined by the fluorescence produced by enzymatic cleavage of the APase substrate 4-methylumbelliferyl phosphate, reported as fluorescence units/min/ml FIG. 3: Graph showing a highly significant, positive linear correlation between APase activity in potable hot water, as determined by the fluorescence produced by enzymatic cleavage of the APase substrate 4-methylumbelliferyl phosphate, reported as log 10 (fluorescence units/hour/100 ml) and log 10 (fluorescence units/30 minutes/250 ml) respectively, and HPC as reported by log 10 (cfu/ml water sample).

Figure 4:
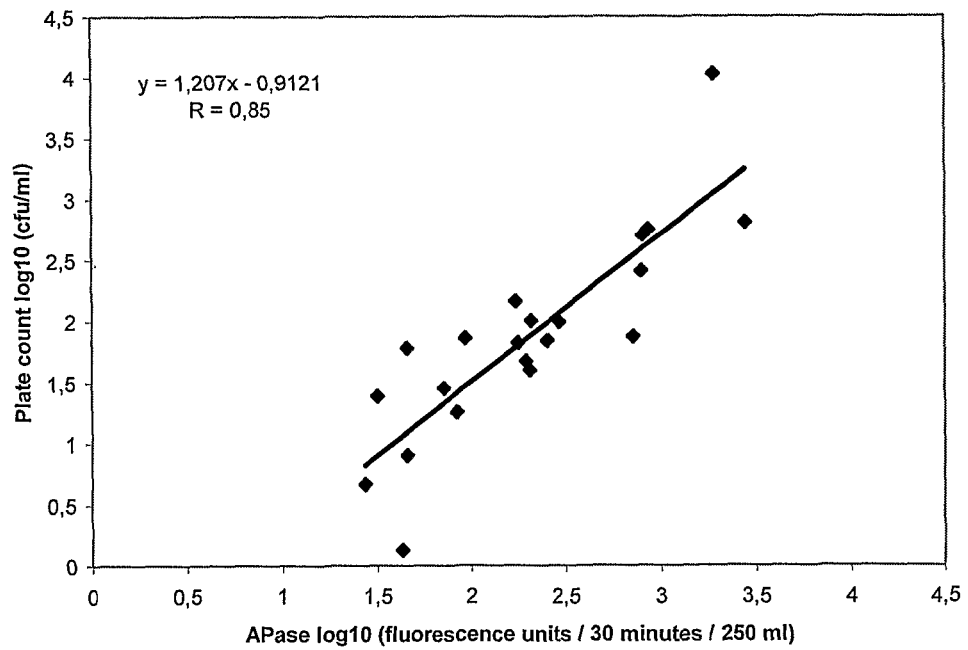

FIG. 4: Graph showing a highly significant, positive linear correlation between APase activity in drinking water, as determined by the fluorescence produced by enzymatic cleavage of the APase substrate 4-methylumbelliferyl phosphate, reported as log 10 (fluorescence units/hour/100 ml) and log 10 (fluorescence units/30 minutes/250 ml) respectively, and HPC as reported by log 10 (cfu/ml water sample)

Figure 5:
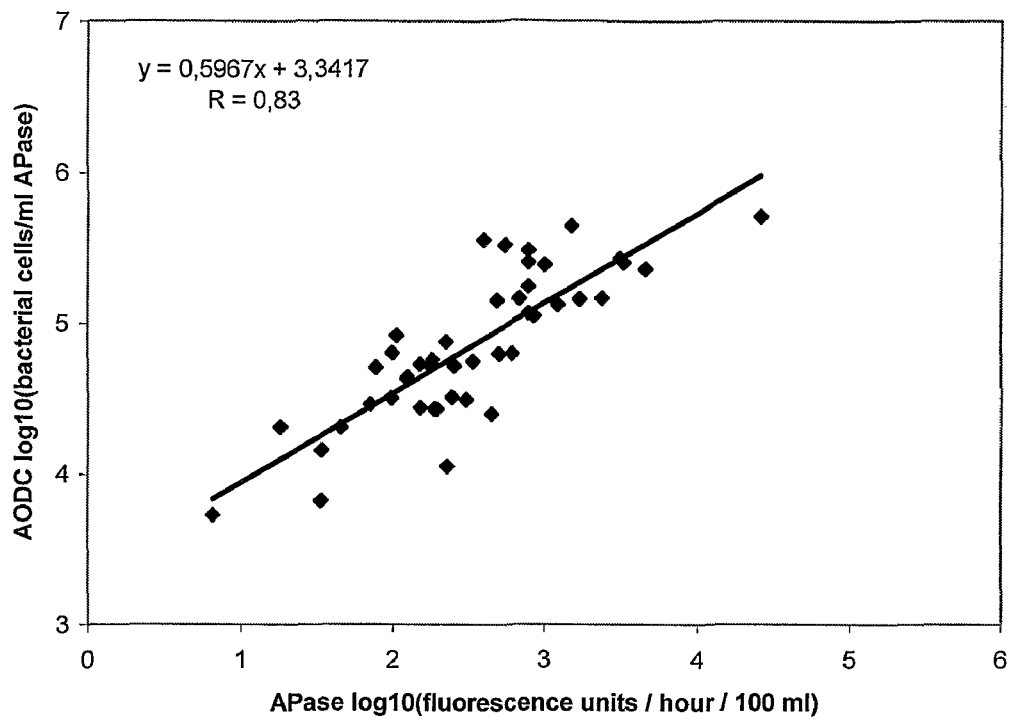

FIG. 5: Graph showing a highly significant linear correlation between APase activity in potable hot water, as determined by enzymatic cleavage of the APase substrate 4-methylumbelliferyl phosphate, reported as log 10 (fluorescence units/hour/100 ml), and Acridine Orange direct counts (AODC) reported as log 10 (bacterial cells/ml).

Figure 6:
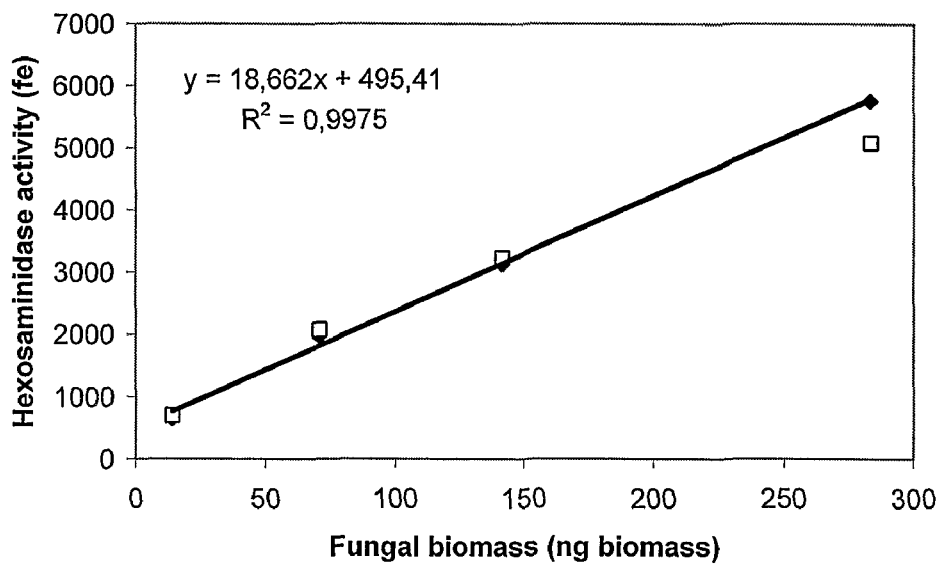

FIG. 6: Graph showing a highly significant linear correlation between spore biomass (measured in ng) of the fungus *Penicillium commune* and N-acetylhexosaminidase enzyme activity (as measured by enzymatic cleavage of the substrated 4-methylumbelliferyl-β-N-acetylglucosaminide).

DETAILED DISCLOSURE OF THE INVENTION

In the following, a number of definitions will be presented in order to define the metes and bounds of the present invention.

As used herein, the term "contaminants" relates to undesired constituents of biological origin in a sample. Non-limiting examples of contaminants are microorganisms, both pathogenic as non-pathogenic, but also fragments of such microorganisms. Non-pathogenic contaminants may be undesired because they are detrimental to the quality of a product when they appear therein (examples are contaminating microorganisms in a controlled fermentation, contaminating microorganisms in food products that influence taste and appearance, etc).

A "viable" microorganism is in the present context a microorganism or spore that under the right set of circumstances is or can become metabolically active. The term thus includes within its scope microorganisms that can readily cultured, but also those that will only multiply under circumstances that are difficult to reproduce in culture.

The term "filter" is in the present context a device that excludes passage of particles larger than a certain size. However, the term can also embrace a device that excludes passage of material that has a significant binding specificity towards a binding partner (such as a receptor, an antibody or fragments thereof). Therefore, the term also embraces devices not normally regarded as "filters", e.g. membranes in centrifuges and ultracentrifuges, membranes impregnated with specific binding partners such as antibodies or other specifically binding substances. Specialised "filters" contemplated by the present invention thus also include columns for affinity chromatography—the important features of a "filter" according to the present invention are that it can retain contaminants of interest and allow a subsequent in situ reaction between a substrate and an enzyme specific for the contaminants so that a subsequent measurement of a detectable moiety derived from the substrate can be readily performed, cf. below.

The term "substrate" means a chemical agent that undergoes an enzyme-catalyzed conversion in its chemical structure.

The term "detectable moiety" denotes a chemical entity which is the result of an enzyme-catalyzed conversion of a substrate, where the chemical entity comprises a physical or chemical characteristic which can be detected and which is not detectable in the substrate. Examples are fluorescent moieties, luminescent moieties, and moieties that bind with high specificity to a binding partner.

The term "signal" is intended to denote the measurable characteristic of a detectable moiety as it is registered in an appropriate measuring system.

Preferred Embodiments of the Method of the Invention

The contaminants are typically selected from the group consisting of bacteria; fungi, such as filamentous fungi and yeast; algae; protozoans; spores from bacteria; fungal spores; and pollen, and fragments thereof. It should be needless to point out that not all of these contaminants are pathogenic, but that their presence in some environments are highly undesirable or even harmful. The presence of contaminating microorganisms in industrial fermentation is one example amongst many, where the economic and practical impact of the presence of contaminants is huge, but also in food production and in production of products that owe their value to aesthetic feature, contaminants may be the cause economic loss.

Fragments of microorganisms and spore have proven to be trigger agents for serious airway diseases such as asthma—even though such fragments (that typically consist of dead bacteria or fungi that are more or less disrupted) are not viable, they may nevertheless be pathology-related to an extent that warrants their detection and removal.

The method of the invention can be applied to samples from various sources, the only rule being that it must be possible to integrate the contaminant-containing sample into a medium, the properties of which allows that it can be passed through a filter.

Conveniently, the medium is a liquid medium. Non-limiting examples include environmental water, drinking water, hot water, industrial water, process water, "cleaning in place" water, pharmaceutical water, a liquid extract of a solid material, a suspended or solubilised surface sample, and liquid industrial products such as cosmetics, pharmaceuticals, and foodstuffs.

Some of these liquid media are in the form of direct, untreated samples from the environment or system of interest. Other samples need to be handled in order to produce the liquid medium that enters step a of the method of the invention.

In some cases, it is for instance desirable to subject the medium to a pre-filtration in order to screen out large-size material that might interfere with a subsequent detection. Such a pre-filter should have a pore size, which allows passage of the contaminants but which does not allow passage of larger-sized materials such as irrelevant solid particles. In some embodiments, this two-step filtration can be combined with application of steps b and c of the method of the invention on both the pre-filter and of the filter where the prefiltered sample has been passed through (the primary filter). By doing this, it becomes possible to add the two measurements in order to obtain a measure for the total contamination.

For some types of samples, however, the method of the invention does not need to be supplemented with any such initial steps. Typically, this is the case if the sample in question does not contain any significant amounts of material having a size comparable to or larger than the contaminants of interest in the sample; for instance, many water or air samples will not need any prefiltration when they are derived from systems where a high degree of purity (and hence a low degree of contamination) is the general rule.

A surface sample can be obtained by wiping a predefined area of a surface with a sampling device/apparatus which includes an absorbing or adsorbing surface. The sampling device is then placed in an appropriate container containing a fluid and agitated to induce release of the surface contaminants into a liquid and subsequently the resulting liquid medium is subjected to the method of the present invention.

A sample of extractable solids can be obtained from environmental samples such as soil, sediments, plants, clothing (e.g. sterile garments), furs and feathers etc. Contaminants from such environmental samples are extracted using an extraction liquid and the extraction liquid is subsequently subjected to the method of the invention.

The sample can be a food product, e.g. a heat processed food product, a food component, a feed product and a feed component. Also here, contaminants are extracted by agitation in a liquid to induce release of contaminants into the extraction liquid to allow subsequent use of the method of the invention on the liquid.

It may also be necessary to reduce the viscosity of the liquid medium prior to performing step a. This is the case when the sample is in fact liquid but with such a high viscosity that it will not readily pass through the filter used according to the invention. Viscosity can be reduced in a number of ways: by means of dilution or by means of treatment with a chemical agent such as a solubility enhancing agent or a detergent.

Also gaseous media can be subjected to the method of the invention. By utilising this embodiment of the invention there is e.g. provided an alternative to conventional methods for measurement of contamination of air and other gases—for instance, where many methods currently in use, provide for a general measurement of fungal spores in air (as a service to allergic people) where the spores are counted, the present invention allows for an easy, fast and convenient means to obtain the same type of information in smaller defined environments without the need for specialised equipment—cf. eg. Example 6, where it is shown that spore counts can be determined by means of the present invention.

So, the gaseous medium can be air, such as air from a sterile facility, a laminar air-flow device or environmental air but also gasses that are used in sterile settings or for direct application to hospitalised patients can be subjected to the method of the invention.

In order to obtain samples from gasses, several methodologies can be applied. One is to simply use the sterile filter in step a in the sampling phase by forcing the gaseous medium through the filter, and then subsequently applying the subsequent steps b and c—the properties of the filter should in such a case be suitable for obtaining samples from gasses and the skilled person will without any problems be capable of selecting a suitable filter; one widely used device for obtaining gas and air samples is AIR-O-CELL® filter cassettes and the use of these are also contemplated in the context of the current invention. Alternatively, the gas is passed through a liquid trap facilitating accumulation of microbes in the liquid and subsequently subjecting this liquid to the method of the invention. In this case, the sample is gaseous, but the medium is in fact liquid.

The filter will normally have a pore size small enough so as to retain substantially all contaminants in the medium. That is, all contaminants of interest. In embodiments of the present invention where it is only of interest to prepare the sample to allow detection of certain contaminants (e.g. not the above-mentioned fragments of bacteria, fungi or spores) the pores can be set to a size that will allow such contaminants to pass through the filter. However, since there are large differences between e.g. protozoan cells and certain bacteria, the pore size of the filter can vary. Also, in order to "catch" contaminants having defined sizes, the method of the invention can be run in several parallel tracks, each using its own pore size in step a; for example, simple subtraction of two measurements obtained from different pore sizes will provide information of the presence of contaminants having a size in the interval between the two pore sizes.

Consequently, it is preferred that the pore size is at most 20 µm, such as at most 15, at most 10, at most 5, and at most 3 µm. For retaining spores or fragments of microorganisms, even smaller pore sizes are preferred.

Further, in many embodiments, the pore size should be large enough to let the detectable moiety pass through the filter; this is of essence when a subsequent detection is performed on the liguid medium which has been evacuated by forcing it through and away from the filter. In this context, the pore size is at least 0.1 µm (but may be larger such as at least 0.22 µm or at least 0.45 µm), but again, the suitable pore size depends on the choice of detectable moiety.

The at least one substrate used according to the invention may conveniently produce the detectable moiety by being cleaved (or otherwise chemically converted) by an enzyme that is characteristic for the contaminants. By this is meant that the enzyme in question is biochemically active in the contaminants that it is the objective to determine. It should be borne in mind that the present invention allows for both detection of total contamination and for detection of contamination with certain subsets or species of contaminants. In the first case, it will be convenient to use a substrate that is converted by a phylogenetically preserved enzyme, i.e. an enzyme or enzyme activity that exists in highly homologous form in practically all contaminants of biological origin, i.e. in most living or viable microorganisms. In the latter case, it will be convenient to use a substrate that is converted by an enzyme that is highly specific for the relevant contaminants. At any rate, the enzyme is typically selected from the group consisting of carbohydrases, proteases, lipases, esterases, amidases, sulfatases, nucleases, and phosphatases such as alkaline phosphatase.

In preferred embodiments, the enzyme that processes the substrate is expressed constitutively by microorganisms. This has the advantage that induction of enzyme production in the contaminants should be unnecessary—it is further relevant to point out that induction of enzyme activity could be a source of error and uncertainty because control over the induction might be difficult to achieve.

Hence, enzymes which can be used in the present method include those naturally produced in a microbial/bacterial cell and in accordance with the invention, detectable enzymatic activities are preferably activities that are expressed constitutively, expressed in all growth phases of the microbial target population/bacteria and/or expressed independently of the physiological state of the microbial target population/bacteria. The enzymatic activity may be intracellular and/or extracellular. The method can thus include the detection and quantification of an enzymatic activity selected from enzymes hydrolysing substrates providing essential nutritional elements for the growth of the target microbial population/bacteria. In the present context the expression "essential nutritional elements" indicate nutrients as defined in e.g. Brock et al., Biology of Microorganisms, Prentice-Hall, Inc., Englewood Cliffs, N.J., USA; Thus essential nutritional elements include nutrients, without which a cell cannot grow and include macronutrients as well as micronutrients. Accordingly the present method can be based upon detection of a microbial/bacterial enzyme involved in e.g. carbohydrate, protein, phosphate and sulphate metabolism. A presently preferred embodiment of the method is, as will appear from the examples, detection of microbial phosphatase enzymes. In particular it is interesting to detect alkaline phosphatase involved in phosphate metabolism including the hydrolysis of phosphate esters, including esters of primary and secondary alcohols, sugar alcohols, cyclic alcohols, phenols and amines, liberating inorganic phosphate. The enzyme also hydrolysis polyphosphates $PP_1$ and the transfer of a $PO_4^{3-}$ group from $PP_1$ (and from a number of nucleoside di- and triphosphates and from mannose-6-phosphate) to glucose, forming glucose-6-phosphate. As will appear from the examples, the alkaline phosphatase activity measurements according to the present invention provide a robust measurement of microbial numbers.

Preferred substrates are fluorogenic or chromogenic substrates producing blue, green and red products (fluorescent or luminescent etc.) as the detectable moiety. Detection of light emission is a highly convenient and fast way of obtaining information of the presence of relevant moieties. Useful substrates in this context are disclosed in Molecular Probes: Handbook of fluorescent probes and research products, ninth edition, author: Richard P. Haugland, chapter 10, pages 397-448.

It is especially preferred to use substrates selected from the group consisting of 5-bromo-4-chloro-3-indolyl phosphate disodium salt; 9h-(1,3-dichloro-9,9-dimethylacridine-2-one-7-yl) phosphate ammonium salt; fluorescein diphosphate tetraammonium salt; a methylumbelliferyl derivative such as 6,8-difluoro-4-methylumbelliferyl phosphate, 4methylumbelliferyl phosphate dicyclohexylammonium salt trihydrate, 4-methylumbelliferyl phosphate free acid; 4-methylumbelliferyl phosphate dilithium salt, 4-methylumbelliferyl-β-N-acetylglucosaminide, and trifluoromethylumbelliferyl phosphate; salts of 4-nitrophenyl phosphate; and resorufin phosphate.

At any rate, regardless of the substrate chosen, the detectable moiety should preferably be detectable in an amount of at the most 100 picomoles, preferably at the most 50 picomoles, more preferably at the most 20 picomoles and even more preferably at the most 10 picomoles and most preferably at the most 1 picomoles. The lower the detection limit is for a particular selectable moiety, the higher is the sensitivity of the method of the invention.

According to the invention, it is possible to use one single substrate, but it is also possible to use at least two substrates that produce detectable moieties providing signals that can be combined into one single measured signal value. By this is meant that the signal obtained from these moieties can be measured within the same measurement window and therefore be integrated into one single measurement (a simple example would be that the moieties are identical even though they originate from conversion of different substrates with different enzymes). Thus, this is a practical means for obtaining information on the total contamination in the sample, especially in the cases where it is not feasible to use one single substrate in order to obtain this information.

It is also possible to use at least two substrates that produce detectable moieties providing distinguishable signals. This provides the advantage that several different groups of contaminants can be determined individually.

One very attractive feature of the present method is that it allows for better determination of viable microorganisms. In a number of prior art methods, the steps including cultivation have the drawbacks that they may not allow certain microorganisms to grow and in fact may even kill certain microorganisms—it may simply be impossible to find growth conditions that is capable of growing all microorganisms up to a detectable level, and therefore the relative distribution of microorganisms before and after culture are non-identical. The prior art measurements therefore do not provide a precise determination of all relevant microorganisms in a sample, but only of those that are cultivable under a given set of circumstances. The present invention does not suffer from this drawback, since the concentration step does not favour or disfavour any contaminants and since the subsequent step of reacting the substrate with the sample medium has no negative impact on any microorganisms in the medium. Therefore, it is preferred that the contaminants are viable microorganisms (or, in other words, that the final result from a measurement on a sample that has gone through step c is a measurement that reflects viable microorganism content.

In order to obtain a reliable measurement of viable microorganisms, the above-mentioned substrates should therefore be selected so as to use those that are converted by enzymes charactertistic of viable microorganisms—one example could be a constitutively expressed enzyme having a high turnover in a metabolically active microorganism.

In the practice of the invention, it is desirable that the amount of substrate in the liquid vehicle does not limit the rate of production of the detectable moiety, since this has the consequence that only the amount of converting enzyme (and hence the amount of contaminants) will set the rate of production. Typically, the substrate/enzyme combination will be chosen so as to ensure that the rate of production of the detectable moiety is a function (preferably linear) of the quantity of contaminants in the known volume of the medium.

In many cases it will be relatively simple to ensure that the amount of detectable moiety which is produced can be translated into a "contaminant number". It may e.g. suffice to provide a qualitative result (of the type "contamination" or "no contamination") because it is merely of interest to determine whether or not a certain threshold value has been exceeded. In other cases, knowledge of the sample type and the system from where it is derived will ensure that one single pass of the method of the invention provides for a precise determination of the contamination count—it is simply a question of ensuring a surplus of substrate in step b so that the enzyme is saturated.

It may be necessary, however, to run the method in parallel so as to pass several different volumes of medium through filters in step a, so as to ensure that at least one of the volumes contains a suitable number of contaminants. An alternative to this is to take several samples of medium having the same volume in step a, and thereafter adding different amount of substrate in step b.

The period of time referred to in step c is the time interval which allows formation of sufficient amounts of the detectable moiety so as to render detection thereof possible. This time interval is conveniently less than 24 hours, but normally much shorter, such as at the most 12, 11, 10, 9, 8, 7, 6, 5, 4, 3, 2, and 1 hours. Normally the time interval will not be less than 5 minutes and it is in most cases not less than 20 minutes.

In preferred embodiments of the present invention, the filter is part of a closed, sterile filter device. The sterility of the filter device ensures that it will not affect the signal to noise ratio in a subsequent measurement, because it does not contribute with contaminants itself. The closed nature of the device serves the same purpose, but also adds to the ease of use of the method of the invention, because the filter unit facilitates easy, practical and sterile handling of the sample.

Preferred devices are disposable closed, sterile filter devices, especially those that integrate the filter and a filter housing into one irreversibly closed structural unit; such filter devices cannot be opened without damaging the filter housing—they are commercially available such as those used in the examples herein. Because of their small size (typically the longest cross-sectional axis of the closed, sterile filter device does not exceed a length of 10 cm, but smaller filter devices exist that do not exceed a length of 9 or 8 or 7 or 6 or even 5 cm) they are very well-suited for on-location sample preparation. A sterile filter device can be selected from commercially available closed/sealed filter units for filtration of liquids. The membrane material can be selected from any available membrane material including low protein binding DURAPORE® (PVDF) membranes, nylon membranes, low protein binding hydrophilic LCR (PTFE) membranes, cellulose acetate etc. A presently preferred embodiment of the method according to the invention is the use of EXPRESS® PES membrane.

It is possible to use filters equipped with a window that e.g. allows fluorescence measurements to be performed directly on the liquid vehicle inside the filter housing—this embodiment of the invention is especially preferred in settings where it is of interest to continuously monitor the conversion of the substrate to release the detectable moiety, cf. below.

In many embodiments of the present invention the interaction in step c is terminated by interrupting the contact between the substrate and the contaminants. This interruption can be obtained by evacuating the liquid vehicle from the filter device while retaining the contaminants in the filter device. Simply pouring or sucking the liquid from the filter into a container free from contaminants is one way of achieving this result, but it is preferred to evacuate liquid vehicle from the filter device in the direction from the influent to the effluent side of the filter, typically done by either applying an elevated pressure on the influent side of the filter or by applying a lowered pressure on the effluent side of the filter. The elevated pressure can be obtained by pressing air or a known volume of a liquid (e.g. a suitable buffer or other solvent such as water) through the filter from the influent side.

It is also possible to terminate the interaction in step c is terminated by other means: it may be terminated on the filter, for instance by physically or chemically inactivating the substrate or the enzymes.

Finally, according to the invention it is also possible not to terminate the interaction at all (relevant in systems where the conversion of the substrate is surveyed periodically or continuously).

Detection Phase

The invention also comprises, after step c, a further step d) that entails detecting, quantitatively or qualitatively, the detectable moiety in the liquid vehicle and correlating the detection of the moiety to the amount or presence of contaminants in the sample.

Such detection may be performed in a number of conventional ways generally known to the person skilled in the art.

Besides being based on the detection of a microbial/bacterial enzymatic activity correlated with the quantity of e.g. the viable microbial target population/bacteria, the present method includes any other assay procedure permitting the detection of enzymes which are correlated with the quantity of the contaminants. Such procedures include as examples detecting the amount of microbial/bacterial enzyme immunologically and the detection of DNA and/or RNA sequences coding for the enzymatic activity of interest. Such procedures can be based on methods well-known in the art and include e.g. the use of antibodies, optionally labelled with detectable moieties and the use of oligonucleotide probes that hybridize selectively to the DNA or RNA sequences.

The determination may be immunological or by any other suitable method that detects interaction between the detectable moiety and a specific binding partner (that is: receptor interactions, antibody or antibody fragment interactions, quenching or enhancement reactions where the detectable moiety quenches or enhances a standard signal through some kind of interaction, etc). However, it is preferred that detection in step d is performed by measuring fluorescence characteristic of the detectable moiety. This is a rapid, reliable and easy-to-use method that does not require any particular skills from the person who handles the measurement.

As mentioned above, the fluorescence in step d can be measured directly on the liquid vehicle without an interruption of the contact between the liquid vehicle and the contaminants. Typically, this will be done when the conversion of the substrate is surveyed continuously or several times so that a relationship over time and amount of detectable moiety can be established—if this relationship is linear, a given the fluorescence value for a given time point can be easily correlated to a standard curve over fluorescence vs. contaminant number.

Measurement of fluorescence is a technique well-known in the art, and requires excitation of a fluorophore with electromagnetic waves (typically ultraviolet or visual light) having a shorter wavelength than the fluorescent emission from the excited fluorophore. The excitation and fluorescence wavelengths are specific for each fluorophore, and the skilled person will know how to choose suitable wavelengths for both purposes.

In general it is preferred that the correlation in step d comprises the use of a pre-determined standard curve that expresses the relationship between the amount of contaminants and the amount of the detectable moiety under standard conditions (such as reaction time, temperature, etc).

According to the invention, the detection may be performed in a microtiter system (especially suited when the detectable moiety is determined via its interaction with another substance such as an antibody). In special versions of this embodiment, the liquid vehicle is passed directly from the effluent side of the filter to the microtiter plate, an effect that can be achieved by integrating the filter with the microtiter plate.

Enhancement of Signal

It may be advantageous to subject the contaminants to a signal-enhancing influence, either prior to step a or in step b—this may increase the overall sensitivity in a subsequent detection or favour subsequent detection of specific types of contaminants, or reduce detection of specific types of contaminants.

Such a signal-enhancing influence is typically selected from an enzyme-enhancing substance, a selective temperature or temperature range, a selective pH, a selective salt concentration, a non-selective growth-enhancer, and a selective growth-enhancing substance. The person skilled in the art is aware of the various possibilities available and will be able to select these in relation to the particular sample, contaminant of interest, substrate/enzyme combination and detection method.

It is also possible to enhance the signal by an incubation of the medium prior to step a. This incubation preferably entails
  treatment with an enzyme inducing substance thereby enhancing the detection of the detectable moiety (and thus a general enhancing effect because conversion of substrate is promoted), and/or
  subjecting the medium to a selective substance for yeast, fungi or bacteria (this has the effect of favouring detection of certain contaminants), and/or
  subjecting the medium to a non-selective growth-enhancer for microorganisms (also a general enhancing effect since the total number of contaminants are thereby increased/propagated—this option, however, should be avoided if the desired result must reflect the "true" number of viable microorganisms in the sample, cf. the reasoning above), and/or
  subjecting the medium to a substance capable of extracting cellular enzymes (comparable to the first alternative because it also promotes the conversion of substrate in step b).

Kit of the Invention

The present invention also contemplates a kit for determination of contaminants in a medium, the kit comprising
  at least one sterile filter device comprising a filter with a pore size sufficiently small to retain the contaminants on the filter's influent side,
  means for passing a known volume of medium through the filter (e.g. a syringe),
  an agent (e.g. a substrate as taught above) that upon interaction with the contaminants will release a detectable moiety, the amount of which can be correlated with the amount of contaminants that have interacted with the agent, and
  instructions that sets forth steps for a) obtaining a known volume of medium and passing it through the sterile filter device, b) contacting the influent side of the filter with the agent, c) allowing the agent to interact with contaminants that might be on the influent side of the filter, and d) quantitatively detecting the detectable moiety.

All the features characterizing this particular kit are described in detail above, meaning that the disclosures above relating to sterile filter devices, agents that produce a detectable moiety etc. apply mutatis mutandis to the kit of the invention and can be used as constituents therein, and meaning that the instructions will correspond to the teachings herein relating to the exercise of the method of the invention, these teachings applying mutatis mutandis to the kit of the invention.

PREAMBLE TO EXAMPLES

Materials and Methods
Media Used
R2A Agar contained (g/litre): Yeast extract 0,5; Proteose Peptone 0,5; Casein Hydrolysate 0,5; Glucose 0,5; Starch soluble 0,5; Sodium Pyruvate0,3; di-Potassium hydrogen phosphate 0,3; Magnesium sulphate 0,05; Agar-agar 12,0.
Yeast extract agar (g/litre): Tryptone (peptone from casein, pancr.) 6,0; Dehydrated yeast extract 3,0; Agar-agar 15,0.
Potable water/hot water media (g/litre): 0.125 Yeast extract.
Dilution media (g/litre); Sodium Chloride 8,5; Peptone (from casein, pancr.)1,0.
All chemicals unless otherwise stated were obtained from Merck KGaA, Darmstadt, Germany.
Enumeration of Cultivable Bacteria Enumeration of cultivable microorganisms, heterotrophic plate count (HPC), in drinking water was performed according to European Standard DS/EN ISO 6222. The samples were transferred to acid rinsed/autoclaved blue cap bottles and stored at 5° C. prior to analysis. All samples were analysed within 4-5 hours of sampling. A volume of raw test sample or peptone diluted test sample was placed in a petri dish. Then 15-20 ml of the molten yeast extract medium was added and mixed carefully by gentle rotation. The medium was then allowed to set. The plates were inverted and incubated at 22±2° C. for 68±4 hours and 36±2° C. for 44±4 h. The results are expressed as the number of colony forming units per millilitre water sample (cfu/ml).

Enumeration of cultivable microorganisms in potable hot water was conducted by a commercial lab (Eurofins, Denmark) according to standard operating procedures (Danish Standard DSF5984). The results are reported as cfu/ml water samples at four temperatures of incubation (37, 44, 55 and 65° C.). The incubation with the highest number of estimated cfu/ml was used in data analysis.

Direct Count of Bacteria Using Acridine Orange Stain (AODC)

Total bacterial counts were obtained using the acridine orange direct count (AODC). Aliquots were filtered on black NUCLEPORE™ polycarbonate 0.2-μm-pore-size filters at max 150 mm Hg. The filters were then washed with two volumes of 8 ml buffer (Citrate-phosphate, pH 5,2). Subsequently the filters were stained for 3 min with acridine orange (final concentration 0.02%), then washed twice with 3 ml of sterilized MILLI-Q® water and mounted on microscope slides. Filters were analyzed using epifluorescence microscopy. For each slide at least 10 microscope fields were observed and at least 400 cells were counted per filter. The number of bacteria was calculated as number of bacterial cells per ml test sample.

Determination of Enzyme Activity in a Liquid Test Sample using a 4-Methylumbelliferyl-Labelled Enzyme Model Substrate.

A liquid test sample is filtrated through a 0.22 μm express 33 mm sterile MILLEX® syringe driven filter unit (Millipore Corporation, Bedford, Mass. U.S.A). Using a reusable plastic syringe, the filter unit is subsequently saturated with an appropriate buffer containing enzyme substrate. The filter is incubated for a fixed time period. The incubation mixture is then washed out using 2 ml of a Glycine-NaOH buffer at pH 10.6 or obtained directly from the filter unit by applying air pressure using a reusable plastic syringe. An aliquot is collected with a pipette and transferred to a 10×10 mm plastic fluorescence cuvette (Sarstedt, Germany) or a 100 microlitre cuvette (Turner Biossystems, USA), respectively. The fluorescence output is measured on a customized MYCROMETER™ fluorometer (Turner Biosystems, USA) at an excitation wavelength of 365 nm and emission wavelength of 465 nm. The enzyme activity is reported as the fluorescence produced by the fluorophore 4-methylumbelliferone released upon enzymatic cleavage of the 4-methylumbelliferyl derivative. The activity is reported as fluorescence units/time unit/ml.

Example 1

Linearity between APase Activity and Bacterial Numbers in a Drinking Water Dilution Series Drinking water was sampled from tap in the MYCOMETER™ laboratorium and yeast extract was added to a final concentration of 125 mg/l. The sample was then incubated at ambient temperature. Bacterial growth was monitored by OD 620 measurements on a spectrophotometer. When the bacterial growth reached late log phase (OD=0.04) the drinking water was sampled for determination of heterotrophic plate counts (HPC). Aliquots of the drinking water were diluted 100, 250, 500, 750 and 1000 fold with filtrated autoclaved drinking water. Alkaline phosphatase (APase) activity was then determined in triplicate for each dilution according to the standard procedure described in the materials and methods section above.

Six replicate determinations of HPC in the incubated water sample averaged $77 \times 10^5$ cfu/ml. This HPC result was used to calculate the cfu/ml for each dilution of the incubated water sample. FIG. 1 demonstrates the linearity between APase activity and HPC, calculated from the drinking water dilutions. The data from experiment 1 was used to calculate the minimum detectable bacterial number in a drinking water sample. The minimum number of bacteria detectable was 21 cfu/ml drinking water sample with the standard procedure described for this invention and calculated from the data in experiment 1.

By simply increasing or decreasing the time of contact between the sample and the enzyme substrate and/or by increasing or decreasing the amount of water filtrated the detection limit can be increased or decreased according to demand or requirement. As an example, 1 bacterium/ml drinking water sample can be detected by filtrating 1 litre drinking water sample and incubating for 2.6 hours. The results demonstrate the high sensitivity and reproducibility of APase activity determinations as well as a strong linear relationship between APase activity ($r=0.99$, $p<0.001$) and a high range of calculated bacterial concentrations. Also the data demonstrate that the sensitivity of the method can be increased by simply increasing sample volume.

Example 2

Linear Increase of APase Activity with Incubation Time in a Drinking Water Sample Added a Minute Amount of Yeast Extract Drinking water was sampled from tap in the MYCOMETER™ laboratorium and yeast extract was added to a final concentration of 125 mg/l. The sample was then incubated at ambient temperature. Bacterial growth was monitored by OD 620 measurements on a spectrophotometer. When the bacterial growth reached late log phase (OD=0.04) water was sampled for determination of Apase activity according to the standard procedure described in the materials and methods section. The drinking water sample was diluted 100 fold with filtrated and autoclaved drinking water. APase activity was then determined in triplicate with varying incubation times of 15, 30, 45 and 60 minutes. FIG. 2 shows a scatter plot of APase activity vs. incubation time. The results demonstrate the linear relationship between incubation time and APase activity. Also the results demonstrate that the sensitivity of the method can be increased by simply increasing the time of contacting the sample with the substrate molecule.

Example 3

Figure 3:
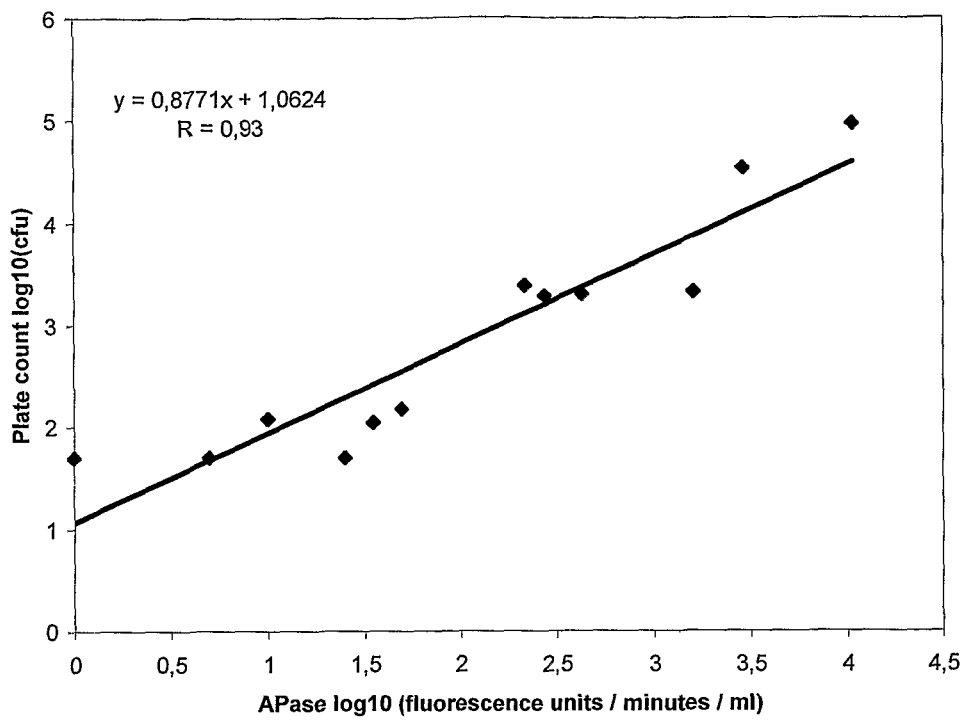

Correlation Between APase Activity and Estimated Eolony Forming Units of Culturable Bacteria in Potable Hot Water Water samples were obtained from six water outlets in a hospital over a period of one year. The water samples were analyzed for APase activity within 24 hours. HPC counts were performed by a commercial laboratory according to Danish Standard DSF 5984 described in the materials and methods section. FIG. 3 shows the scatter plot of APase activity and HPC. The result demonstrates a positive linear correlation (r=0.93, p<0.001) between APase activity and HPC in potable hot water.

Example 4

Correlation Between APase Activity and Estimated Colony Forming Units of Cultivable Bacteria in Drinking Water Samples were obtained from a range of drinking water systems including private homes businesses and public buildings. Analyses were performed within 2-12 hours of sampling. The drinking water test samples were kept at 5° C. until analysis. Enumeration of cultivable bacteria and determination of APase activity was performed according to the standard procedures described in the material and methods section above. FIG. 4 shows a scatter plot of APase activity and HPC in drinking water samples. The result demonstrate a positive linear correlation (r=0.85, p<0.001) between APase activity and HPC.

Example 5

Correlation Between APase Activity and Acridine Orange Direct Count (AODC) in Potable Hot Water Samples were obtained from a range of drinking water systems including private homes, businesses and public buildings. Analysis was performed within 24 hours of sampling. AODC was performed as described in the materials and methods section. FIG. 5 shows a scatter plot of APase activity and AODC in potable hot water. The results demonstrate a strong positive linear correlation (r=0.78, P<0.001) between APase activity and AODC.

Example 6

Linearity Between N-Acetylhexosaminidase Activity and Fungal Spore Biomass

A fungal spore suspension was prepared from agar cultures (malt extract agar) with the fungus *Penicillium commune*.

The spore biomass of the suspension was determined by filtering 6 ml of the spore suspension through a pre-weighed nylon membrane filter (0,45 μm) and drying at 60° C. for 24 hours. A dilution series of spore suspensions were prepared in duplicate by transferring 50 μl, 100 μl, 250 μl and 500 μl spore suspension, respectively, to individual culture tubes. The spore suspensions were diluted to a total of 3 ml by adding autoclaved distilled water to each of the culture tubes.

N-acetylhexosaminidase enzyme activity of the spore suspension was analyzed as described in the materials and methods section, with the following modifications: The filter unit was saturated with an appropriate buffer containing the enzyme substrate 4-methylumbelliferyl-β-N-acetylglucosaminide. After incubation, the incubation mixture was obtained directly from the filter unit by applying pressure using a reusable plastic syringe. An aliquot of 100 μl was then alkalized by transfer to a plastic cuvette containing 2 ml of appropriate buffer at pH 10.6.

The strong positive linear correlation (r=0.9975; P<0.001) between spore biomass and N-acetylhexosaminidase activity is shown in the scatter plot FIG. 6.

The invention claimed is:

1. A method for detecting contaminants in a medium suspected of containing such contaminants, the method comprising the consecutive steps of:
   a) passing a known volume of said medium through a filter from an influent side to an effluent side in a filter device thereby concentrating the contaminants on the influent side of the filter in the filter device;
   b) contacting the influent side of the filter in the filter device with a liquid vehicle containing at least one substrate, wherein said at least one substrate through interaction with an enzyme characteristic of the contaminants produces a detectable moiety;
   c) allowing the substrate to interact with the contaminants on the influent side of the filter in the filter device for a period of time, which is sufficient to allow the detectable moiety to be detected in the liquid vehicle;
   d) evacuating the liquid vehicle from the influent side of the filter by forcing the liquid vehicle through to the effluent side of the filter; and
   e) performing a quantitative or qualitative detection of the detectable moiety in the liquid vehicle evacuated in step d and correlating the detection of the moiety to the amount or presence of contaminants in the sample.

2. The method according to claim 1, wherein, prior to step a, the medium is passed through a prefilter that does not retain the contaminants, but retains larger particles.

3. The method according to claim 1, wherein the contaminants are selected from the group consisting of bacteria; fungi; algae; protozoans; spores from bacteria; fungal spores; and pollen, and fragments threof.

4. The method according to claim 3, wherein the fungi is one selected from the group consisting of filamentous fungi and yeast.

5. The method according to claim 1, wherein the medium is a liquid medium.

6. The method according to claim 5, wherein the viscosity of the liquid medium is reduced prior to step a.

7. The method according to claim 6, wherein the viscosity is reduced by means of dilution or by means of treatment with a chemical agent.

8. The method according to claim 7, wherein the chemical agent is one selected from the group consisting of a solubility enhancing agent and a detergent.

9. The method according to claim 5, wherein the liquid medium is selected from the group consisting of environmental water, drinking water, hot water, industrial water, process water, cleaning in place water, a liquid extract of a solid material, a suspended or solubilised surface sample, and liquid industrial products such as cosmetics, pharmaceuticals, and foodstuffs.

10. The method according to claim 1, wherein the medium is a gaseous medium.

11. The method according to claim 10, wherein the gaseous medium is air.

12. The method according to claim 11, where the air is one selected from the group consisting of air from sterile facility, air from a laminar air-flow device and environmental air.

13. The method according to claim 1, wherein the filter has a pore size small enough so as to retain substantially all contaminants in the medium.

14. The method according to claim 13, wherein the filter has a pore size large enough to let the detectable moiety pass through the filter.

15. The method according to claim 14, wherein the pore size is at most 20 µm.

16. The method according to claim 14, wherein the pore size is at least 0.1 µm.

17. The method of claim 1, wherein the at least one substrate produces the detectable moiety by being cleaved by an enzyme that is characteristic for the contaminants.

18. The method according to claim 17, wherein the enzyme is selected from the group consisting of carbohydrases, proteases, lipases, esterases, amidases, sulfatases, nucleases and phosphatases.

19. The method according to claim 18, wherein the enzyme is a phosphatase, and the phosphatase is alkaline phosphatase.

20. The method according to claim 17, wherein the enzyme is expressed constitutively by microorganisms.

21. The method according to claim 17, wherein the at least one substrate is a fluorogenic or chromogenic substrate producing blue, green and red products as the detectable moiety.

22. The method according to claim 17, wherein the at least one substrate is selected from the group consisting of 5-bromo-4-chloro-3-indolyl phosphate disodium salt; 9h-(1,3-dichloro-9,9-dimethylacridine-2-one-7-yl) phosphate ammonium salt; fluorescein diphosphate tetraamonium salt; a methylumbelliferyl derivative; salts of 4-nitrophenyl phosphate; and resorufin phosphate.

23. The method according to claim 22, wherein the methylumbelliferyl derivative is one selected from the group consisting of 6,8-difluoro-4-methylumbelliferyl phosphate, 4-methylumbelliferyl phosphate dicyclohexylammonium salt trihydrate, 4-methylumbelliferyl phosphate free acid; 4-methylumbelliferyl phosphate dilithium salt, 4-methylumbelliferyl-β-N-acetylglucosaminide and trifluoromethlumbelliferyl phosphate.

24. The method according to claim 17, wherein the detectable moiety is detectable in an amount of at the most 50 picomoles.

25. The method according to claim 17, wherein the detectable moiety is detectable in an amount of at the most 20 picomoles.

26. The method according to claim 17, wherein the detectable moiety is detectable in an amount of at the most 10 picomoles.

27. The method according to claim 17, wherein the detectable moiety is detectable in an amount of at the most 1 picomoles.

28. The method according to claim 1, wherein the at least one substrate includes at least two substrates that produce detectable moieties providing signals that can be combined into one single measured signal value.

29. The method according to claim 1, wherein the at least one substrate includes at least two substrates that produce detectable moieties providing distinguishable signals.

30. The method according to claim 1, wherein the contaminants are viable microorganisms.

31. The method according to claim 1, wherein the amount of the at least one substrate in the liquid vehicle does not limit the rate of production of the detectable moiety.

32. The method according to claim 31, wherein the rate of production of the detectable moiety is a function of the quantity of contaminants in the known volume of the medium.

33. The method according to claim 32, wherein the function is linear.

34. The method according to claim 1, wherein several different known volumes of the medium are each passed through a filter in step a, so as to ensure that at least one of the volumes contains a suitable number of the contaminants.

35. The method according to claim 1, wherein the filter is part of a closed, sterile filter device.

36. The method according to claim 35, wherein the closed, sterile filter device is disposable.

37. The method according to claim 35, wherein the closed, sterile filter device integrates the filter and a filter housing into one irreversibly closed structural unit.

38. The method according to claim 35, wherein the longest cross-sectional axis of the closed, sterile filter device does not exceed a length of 10 cm.

39. The method according to claim 1, wherein evacuation is obtained by applying an elevated pressure on the influent side of the filter or by applying a lowered pressure on the effluent side of the filter.

40. The method according to claim 1, wherein detection in step d is performed by measuring fluorescence characteristic of the detectable moiety.

41. The method according to claim 40, wherein the fluorescence in step d is measured directly in the liquid vehicle without an interruption of the contact between the liquid vehicle and the contaminants.

42. The method according to claim 1, wherein the correlation in step d comprises the use of a pre-determined standard curve that expresses the relationship between the amount of contaminants and the amount of the detectable moiety under standard conditions.

43. The method according to claim 1, wherein detection is performed in a microtiter system.

44. The method according to claim 1, wherein the contaminants are subjected to a signal-enhancing influence, either prior to step a or in step b, and
the signal-enhancing influence is one selected from the group consisting of an enzyme-enhancing substance, a selective temperature, a temperature range, a selective pH, a selective salt concentration, a non-selective growth-enhancer and a selective growth-enhancing substance.

45. The method according to claim 44, where the signal-enhancing influence increases the overall sensitivity in a subsequent detection or favours subsequent detection of specific types of contaminants, or reduces detection of specific types of contaminants.

46. The method according to claim 1, wherein step a is preceded by an incubation of the medium.

47. The method according to claim 46, wherein the incubation entails at least one selected from the group consisting of:
treatment with an enzyme inducing substance thereby enhancing the detection of the detectable moiety,
subjecting the medium to a selective substance for yeast, fungi or bacteria,
subjecting the medium to a non-selective growth-enhancer for microorganisms, and
subjecting the medium to a substance capable of extracting cellular enzymes.

48. The method of claim 17, wherein the detectable moiety is detectable in an amount of at the most 100 picomoles.

49. A method for detecting contaminants in a medium suspected of containing such contaminants, the method comprising the consecutive steps of:
  a) passing a known volume of said medium through a filter from an influent side to an effluent side in a filter device thereby concentrating the contaminants on the influent side of the filter in the filter device;
  b) contacting the influent side of the filter in the filter device with a liquid vehicle containing at least one substrate, wherein said at least one substrate through interaction with an enzyme characteristic of the contaminants produces a detectable moiety;
  c) allowing the substrate to interact with the contaminants on the influent side of the filter in the filter device for a period of time between 5-minutes to 24-hours, which is sufficient to allow the detectable moiety to be detected in the liquid vehicle;
  d) evacuating the liquid vehicle from the influent side of the filter by forcing the liquid vehicle through to the effluent side of the filter; and
  e) performing a quantitative or qualitative detection of the detectable moiety in the liquid vehicle evacuated in step d and correlating the detection of the moiety to the amount or presence of contaminants in the sample.

50. The method of claim 49, wherein the period of time is between 20-minutes to 12-hours.

* * * * *

UNITED STATES PATENT AND TRADEMARK OFFICE
CERTIFICATE OF CORRECTION

PATENT NO. : 7,939,285 B2  Page 1 of 1
APPLICATION NO. : 10/591321
DATED : May 10, 2011
INVENTOR(S) : Morton Reeslev et al.

It is certified that error appears in the above-identified patent and that said Letters Patent is hereby corrected as shown below:

On the title page item (75), should read:

Inventors:  ~~Merton~~ Morten Reeslev, Copenhagen Ø (DK);
Morten Miller, Copenhagen Ø (DK)

Signed and Sealed this
Thirteenth Day of September, 2011

David J. Kappos
*Director of the United States Patent and Trademark Office*